US006911621B2

(12) United States Patent
Bhullar et al.

(10) Patent No.: US 6,911,621 B2
(45) Date of Patent: Jun. 28, 2005

(54) BIOSENSOR (75) Inventors: Raghbir S. Bhullar, Indianapolis, IN (US); Douglas P. Walling, Indianapolis, IN (US); Brian S. Hill, Avon, IN (US)

(73) Assignee: Roche Diagnostics Corporation, Indianapolis, IN (US)

( * ) Notice: Subject to any disclaimer, the term of this patent is extended or adjusted under 35 U.S.C. 154(b) by 212 days.

(21) Appl. No.: 10/338,498

(22) Filed: Jan. 8, 2003

(65) Prior Publication Data

US 2003/0094367 A1 May 22, 2003

Related U.S. Application Data

(63) Continuation of application No. 09/704,145, filed on Nov. 1, 2000.

(51) Int. Cl.[7] .................... B23K 26/36; G01N 27/327

(52) U.S. Cl. ................... 219/121.69; 156/272.8

(58) Field of Search ............ 219/121.6, 121.67–121.69, 219/121.72; 204/403.01, 403.02, 403.09, 403.14, 416; 422/50, 55, 58; 156/272.8; 216/65; 427/554–556

(56) References Cited

U.S. PATENT DOCUMENTS

| | | | |
|---|---|---|---|
| 4,081,653 A | 3/1978 | Koo et al. ................... 219/121 |
| 4,131,484 A | 12/1978 | Caruso et al. ................. 134/1 |
| 4,294,679 A | 10/1981 | Maurer et al. .............. 204/195 |
| 4,414,059 A | 11/1983 | Blum et al. .............. 156/659.1 |
| 4,684,437 A | 8/1987 | Donelon et al. ............ 156/643 |
| 4,865,873 A | 9/1989 | Cole et al. ................. 427/53.1 |
| 4,874,500 A | 10/1989 | Madou et al. .............. 204/412 |
| 4,897,173 A | 1/1990 | Nankai et al. .............. 204/403 |
| 4,902,138 A | 2/1990 | Goeldner et al. ............. 374/44 |
| 4,957,582 A | 9/1990 | Columbus ................... 156/332 |
| 4,963,814 A | 10/1990 | Parks et al. ................. 323/274 |
| 4,999,582 A | 3/1991 | Parks et al. ................. 324/438 |
| 4,999,632 A | 3/1991 | Parks ......................... 341/167 |
| 5,018,164 A | 5/1991 | Brewer et al. .............. 372/109 |
| 5,089,103 A | 2/1992 | Swedberg ............... 204/182.8 |
| 5,104,480 A | 4/1992 | Wojnarowski et al. ...... 156/643 |
| 5,120,420 A | 6/1992 | Nankai et al. .............. 204/403 |
| 5,165,407 A | 11/1992 | Wilson et al. .............. 128/635 |
| 5,243,516 A | 9/1993 | White ......................... 364/413 |

(Continued)

FOREIGN PATENT DOCUMENTS

| | | |
|---|---|---|
| DE | 42 33 178 A1 | 4/1994 |
| EP | 0 376 721 | 7/1990 |
| EP | 0 480 703 A2 | 4/1992 |

(Continued)

OTHER PUBLICATIONS

Tender, L. et al., Electrochemical Patterning of Self–Assembled Monolayers onto Microscopic Arrays of Gold Electrodes Fabricated by Laser Ablation, *Langmuir*, 1996, 12, 5515–5518.

Tahhan, Isam, "Biocompatible Microstructuring of Polymers and Electrodes with an Excimer Laser", MEDICS Workshop 2000 Speakers Abstracts, 2 pp.

Sheppard, Jr. et al. "Electrical Conductivity Measurements Using Microfabricated Interdigitated Electrodes", *Anal. Chem.*, 1993, 65, 1199–1202.

(Continued)

*Primary Examiner*—Samuel M. Heinrich
(74) *Attorney, Agent, or Firm*—Jill J. Woodburn (57) ABSTRACT

A method of forming a biosensor is provided. The method includes providing a substrate and a cover including first and second surfaces, positioning a reagent on the substrate, carving a channel by laser ablation in the first surface, and coupling the first surface of the cover to the second surface. The channel includes a first portion having a first height and a second portion having a second height that is less than the first height.

20 Claims, 4 Drawing Sheets

U.S. PATENT DOCUMENTS

| | | | |
|---|---|---|---|
| 5,264,103 A | 11/1993 | Yoshioka et al. | 204/403 |
| 5,266,179 A | 11/1993 | Nankai et al. | 204/401 |
| 5,288,636 A | 2/1994 | Pollmann et al. | 435/288 |
| 5,334,279 A | 8/1994 | Gregoire | 156/630 |
| 5,336,388 A | 8/1994 | Leader et al. | 204/406 |
| 5,352,351 A | 10/1994 | White et al. | 204/406 |
| 5,366,609 A | 11/1994 | White et al. | 204/403 |
| 5,382,346 A | 1/1995 | Uenoyama et al. | 204/403 |
| 5,384,028 A | 1/1995 | Ito | 204/403 |
| 5,390,412 A | 2/1995 | Gregoire | 29/848 |
| 5,391,250 A | 2/1995 | Cheney, II et al. | 156/268 |
| 5,395,504 A | 3/1995 | Saurer et al. | 204/403 |
| 5,405,511 A | 4/1995 | White et al. | 204/153.1 |
| 5,413,690 A | 5/1995 | Kost et al. | 204/403 |
| 5,414,224 A | 5/1995 | Adasko et al. | 174/262 |
| 5,426,826 A | 6/1995 | Fukutomi et al. | 29/848 |
| 5,437,999 A | 8/1995 | Diebold et al. | 435/288 |
| 5,451,722 A | 9/1995 | Gregoire | 174/261 |
| 5,465,480 A | 11/1995 | Karl et al. | 29/825 |
| 5,496,453 A | 3/1996 | Uenoyama et al. | 205/777.5 |
| 5,508,171 A | 4/1996 | Walling et al. | 205/777.5 |
| 5,509,410 A | 4/1996 | Hill et al. | 128/637 |
| 5,512,489 A | 4/1996 | Girault et al. | 205/777.5 |
| 5,575,930 A | 11/1996 | Tietje-Girault et al. | 216/65 |
| 5,576,073 A | 11/1996 | Kickelhain | 427/555 |
| 5,589,326 A | 12/1996 | Deng et al. | 435/4 |
| 5,593,739 A * | 1/1997 | Kickelhain | 427/555 |
| 5,628,890 A | 5/1997 | Carter et al. | 204/403 |
| 5,635,054 A | 6/1997 | Girault et al. | 205/775 |
| 5,682,884 A | 11/1997 | Hill et al. | 128/637 |
| 5,708,247 A | 1/1998 | McAleer et al. | 204/403 |
| 5,739,039 A | 4/1998 | Girault et al. | 436/149 |
| 5,755,953 A | 5/1998 | Henning et al. | 205/778 |
| 5,758,398 A | 6/1998 | Rijnbeek et al. | 29/25.42 |
| 5,759,364 A | 6/1998 | Charlton et al. | 204/403 |
| 5,762,770 A | 6/1998 | Pritchard et al. | 204/403 |
| 5,773,319 A | 6/1998 | Chu et al. | 438/39 |
| 5,798,031 A | 8/1998 | Charlton et al. | 204/403 |
| 5,948,289 A | 9/1999 | Noda et al. | 219/121.69 |
| 5,948,695 A | 9/1999 | Douglas et al. | 436/518 |
| 5,955,179 A | 9/1999 | Kickelhain et al. | 428/210 |
| 5,956,572 A | 9/1999 | Kidoguchi et al. | 438/96 |
| 5,965,001 A | 10/1999 | Chow et al. | 204/600 |
| 6,004,441 A | 12/1999 | Fujiwara et al. | 204/412 |
| 6,068,748 A | 5/2000 | Berger et al. | 204/426 |
| 6,103,033 A | 8/2000 | Say et al. | 156/73.1 |
| 6,134,461 A | 10/2000 | Say et al. | 600/345 |
| 6,165,594 A | 12/2000 | Moh et al. | 428/207 |
| 6,175,752 B1 | 1/2001 | Say et al. | 600/345 |
| 6,203,952 B1 | 3/2001 | O'Brien et al. | 430/17 |
| 6,258,229 B1 * | 7/2001 | Winarta et al. | 204/403.04 |
| 6,287,451 B1 | 9/2001 | Winarta et al. | 205/777.5 |
| 6,299,757 B1 | 10/2001 | Feldman et al. | 205/775 |
| 6,309,526 B1 | 10/2001 | Fujiwara et al. | 204/403 |
| 6,338,790 B1 | 1/2002 | Feldman et al. | 205/777.5 |
| 6,399,258 B2 | 6/2002 | O'Brien et al. | 430/17 |
| 6,662,439 B1 | 12/2003 | Bhullar | 29/825 |
| 6,696,008 B2 | 2/2004 | Bradinger | 264/400 |
| 2001/0006766 A1 | 7/2001 | O'Brien et al. | |
| 2003/0088166 A1 | 5/2003 | Say et al. | |

FOREIGN PATENT DOCUMENTS

| | | |
|---|---|---|
| EP | 0 480 703 B1 | 3/1997 |
| EP | 0 875 754 | 11/1998 |
| EP | 0 964 059 A2 | 12/1999 |
| EP | 1 152 239 A1 | 11/2000 |
| EP | 1 098 000 A2 | 5/2001 |
| EP | 1 195 441 A1 | 4/2002 |
| EP | 1 202 060 A1 | 5/2002 |
| EP | 1 203 956 A2 | 5/2002 |
| EP | 1 203 956 A3 | 5/2002 |
| EP | 1 288 654 A1 | 3/2003 |
| JP | 56100451 | 8/1981 |
| JP | 5-31 5703 | 11/1993 |
| JP | 7-66499 | 3/1995 |
| JP | 7-290751 | 11/1995 |
| JP | 9-260697 | 10/1997 |
| JP | 10-52780 | 2/1998 |
| JP | 10-241992 | 9/1998 |
| JP | 10-275959 | 10/1998 |
| JP | 10-303444 | 11/1998 |
| JP | 11-088784 | 3/1999 |
| JP | 11297890 | 10/1999 |
| JP | 2000-121594 | 4/2000 |
| WO | WO 91/02391 | 2/1991 |
| WO | WO 91/08474 | 6/1991 |
| WO | WO 95/22881 | 8/1995 |
| WO | WO 98/35225 | 8/1998 |
| WO | WO 98/49773 | 12/1998 |
| WO | WO 98/55856 | 12/1998 |
| WO | WO 99/13101 | 3/1999 |
| WO | WO 99/30152 | 6/1999 |
| WO | WO 99/45387 | 9/1999 |
| WO | WO 00/42472 A1 | 7/2000 |
| WO | WO 00/73778 | 12/2000 |
| WO | WO 00/73785 | 12/2000 |
| WO | WO 01/25775 | 4/2001 |
| WO | WO 01/36953 | 5/2001 |
| WO | WO 01/75438 | 10/2001 |
| WO | WO 01/92884 | 12/2001 |
| WO | WO 02/27074 | 4/2002 |
| WO | WO 02/086483 | 10/2002 |

OTHER PUBLICATIONS

Srinivasan R., et al. "Ultraviolet Laser Ablation of Organic Polymers", Chem. Rev., 1989, 89, 1303–1316.

Zongyi, Q., et al. "Excimer Laser Patterning on Thin Polymer Surfaces for Electrochemical Gas Sensors", Polymer Physics Laboratory, Changchun Institute of Applied Chemistry, Chinese Academy of Sciences, Changchun, Peop. Rep. China., Proceedings of the International Conference on Lasers (1999) 21st (Abstract) 1pp.

Vaucher et al. "Laser Direct Imaging and Structuring: An Update", http://www.circuitree.com/CDA/ArticleInformation/features/BNP_Features_Item/0.2133.81173.00.html; posted on: Aug. 1, 2002.

Wu, J. et al. "Single–shot Excimer Laser Ablation of Thick Polymer Resists on Metallic Substrates", AMP Journal of Technology vol. 1 Nov., 1991, 69–79.

Srinivasan, R., "Ablation of Polymers and Biological Tisssue by Ultraviolet Lasers", Science, vol. 234, Oct. 21, 1986, 559–564.

Colon, W., "Microanalysis: Biosensors at the Point of Care", MST News 01/04, pp. 9–11.

Duley, W.W. "UV Lasers: effects and applications in materials science", Chapter 3 Photochemical and photothermal effects, Cambridge University Press, pp. 78–97.

LPKF MicrolineLaser II, LPKF Laser & Electronics AG; LPKF; Art.–Nr. 107645–2 (01/00) (2pp.).

Microline Solutions, LPKF Laser & Electronics AG; LPKF; Art.–Nr. 107658–1 (01/00) (3pp.).

* cited by examiner

BIOSENSOR

CROSS-REFERENCE TO RELATED APPLICATION

This application is a continuation of U.S. Pat. No. 6,540,890 issued on Apr. 1, 2003.

FIELD OF THE INVENTION

The present invention relates to a biosensor and particularly to biosensor that includes a channeled cover.

BACKGROUND AND SUMMARY OF THE INVENTION

Electrochemical biosensors are known. They have been used to determine the concentration of various analytes from biological samples, particularly from blood. Biosensors are described in U.S. Pat. Nos. 5,413,690; 5,762,770; 5,798,031; and 5,997,817, the disclosure of each of which are expressly incorporated herein by reference.

Laser ablation is a known technique that uses a laser to remove a material. See, for example, U.S. Pat. Nos. 5,576,073 and 5,593,739 and International WO98/35225, the disclosure of each of which is expressly incorporated herein by reference. Such known laser ablation systems use a high power excimer laser, such as a krypton fluoride excimer laser with an illumination wavelength of 248 nanometers, to remove surface material.

According to the present invention a biosensor is provided. The biosensor comprises a substrate, a reagent positioned on the substrate, and a cover. The cover includes a first surface coupled to the substrate and a second surface. The first surface has a flow channel carved therein that extends over at least a portion of the reagent.

According to another aspect of the present invention, a biosensor is provided. The biosensor comprises a substrate, a reagent positioned on the substrate, and a cover coupled to the substrate. The cover includes opposite ends, a first surface coupled to the substrate, and a second surface. The first surface has a flow channel carved therein. The flow channel extends between the opposite ends.

In still another aspect of the present invention, a method of forming a biosensor is provided. The method comprises the steps of providing a substrate and a cover that has first and second surfaces, applying a reagent onto the substrate to define a reaction zone, carving a channel in the first surface of the cover, and coupling the cover on the substrate so that the channel extends over at least a portion of the reagent.

Additional features of the invention will become apparent to those skilled in the art upon consideration of the following detailed description of the preferred embodiment exemplifying the best mode of carrying out the invention

BRIEF DESCRIPTION OF THE DRAWINGS

The detailed description particularly refers to the accompanying figures in which.

DETAILED DESCRIPTION OF THE DRAWINGS

A biosensor 10 in accordance with the present invention provides a cover with at least one channel carved therein. The channel may be used in a variety of diagnostic biosensors including, for example, electrochemical and photometric sensors. The purpose of the channel is to provide precise fluidic channels for disposable diagnostic tests with high dimensional precision. Various aspects of the invention are presented in FIGS. 1–9, which are not drawn to scale and wherein like components in the several views are numbered alike.

FIGS. 1–5 illustrate an aspect of the invention in the form of an electrochemical biosensor 10 having a cover 12, a bottom substrate 14, electrically conductive tracks 16, 18, and a reagent 20 extending over a portion of tracks 16, 18. Biosensor 10 is preferably rectangular in shape. It is appreciated, however, that biosensor 10 can assume any number of shapes in accordance with this disclosure. Biosensor 10 is preferably produced from rolls of material, however, it is understood that biosensor 10 can be constructed from individual sheets in accordance with this disclosure. Thus, the selection of materials for the construction of biosensor 10 necessitates the use of materials that are sufficiently flexible for roll processing, but which are still rigid enough to give a useful stiffness to finished biosensor 10.

Cover 12 of biosensor 10 includes a first surface 48 facing substrate 14 and an opposite second surface 50. See FIGS. 1–2. In addition, cover 12 has opposite ends 52, 54 and edges 56, 58 extending between ends 52, 54. End 52 has a generally concave portion 60 that extends between edges 56, 58 in order to accommodate a user's finger. Preferably, cover 12 is formed of a flexible polymer and preferably from a polymer such as a polyester. A non-limiting example of a suitable polymer is 7 mil thick ST505 MELINEX® polyester film commercially available from E.I. DuPont de Nemours, Wilmington, Del. Cover 12 is coupled to substrate 14 by a liquid adhesive. A non-limiting example of such an adhesive is EPO-TEK OH100-4 commercially available from Epoxy Technology, Billerica, Mass. It is appreciated that cover 12 may be coupled to bottom substrate 14 using a wide variety of commercially available adhesives in accordance with this disclosure.

Figures 1, 2:
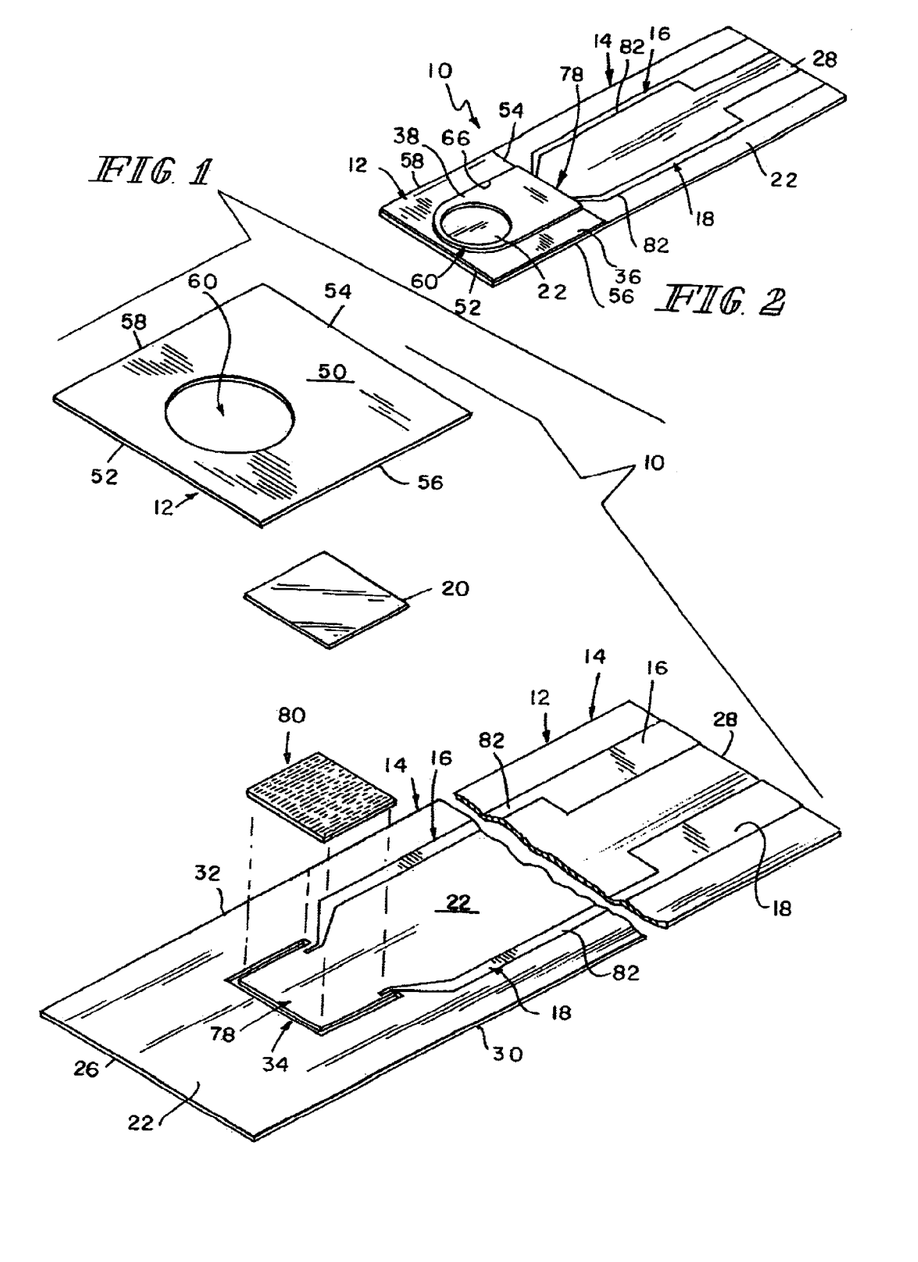
FIG. 1 is an exploded assembly view of an electrochemical biosensor in accordance with the present invention showing the biosensor including a substrate, a reagent, and a cover.
FIG. 2 is a bottom perspective view of the cover FIG. 1.
Figure 3:
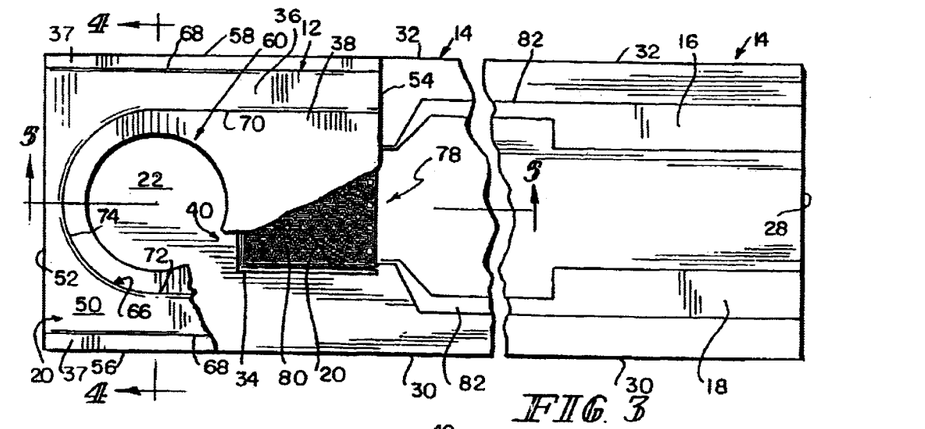
FIG. 3 is an end view of the biosensor of FIG. 1.
Figure 4:
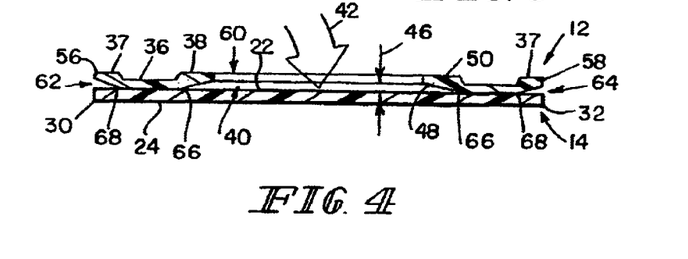
FIG. 4 is a view taken along lines 4—4 of FIG. 1.
Figure 5:
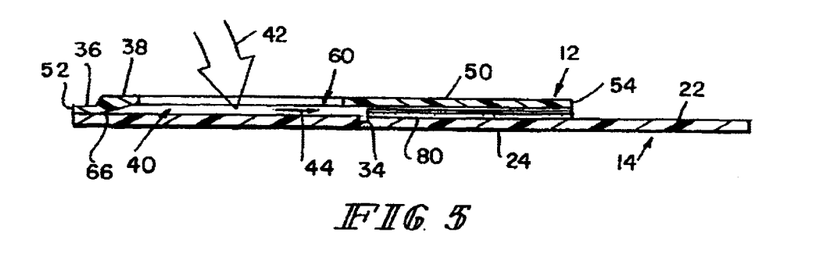
FIG. 5 is a view taken along lines 5—5 of FIG. 1.

Additionally, as shown in FIG. 2, a flow channel 62 is carved in first surface 48 of cover 12. As used throughout the specification and claims, the term "carve" is defined as to make or get by cutting into a surface, thereby hollowing out a pre-determined space in that surface. Channel 62 extends between ends 52, 54. Channel 62 includes a first floor portion 36 and a second floor portion 38. In addition, opposite walls 46 extend from first floor portion 36 and opposite walls 40 extend from second floor portion 38. See FIG. 2. First floor portion 36 and walls 46 define a first portion 72 of channel 62 and second floor portion 38 and walls 40 define a second portion 74 of channel 62. Walls 46 have a first height as shown by arrows 42 and walls 40 have a second height as shown by arrows 44. First height 42 is greater than the second height 44, so that a liquid sample traveling in channel 62 encounters increasing capillary forces as the sample enters second portion 74 of channel 62. Therefore, channel 62 facilitates movement of the liquid sample away from concave portion 60 and toward reagent 20 positioned spaced-apart from end 52.

The height of walls 46 in first channel portion 36 is dependent upon the choice of the overall thickness of cover 12, but generally ranges from about 1 $\mu$m to about 150 $\mu$m. Preferably, the height of walls 46 is from about 75 $\mu$m to about 120 $\mu$m, and most preferably about 84 $\mu$m. The height of walls 40 in second channel portion 38 is also dependent upon the choice of the overall thickness of cover 12, but generally ranges from about 1 $\mu$m to about 75 $\mu$m. Preferably the height of walls 40 is from about 5 $\mu$m to about 50 $\mu$m, most preferably about 25 $\mu$m. The channel portion 38 is approximately 1000 $\mu$m to about 4000 $\mu$m wide, preferably about 2000 $\mu$m to about 3000 $\mu$m wide, and most preferably about 2500 $\mu$m wide. It is appreciated that channel 62 may be formed with a single height or width, or that it may have a variety of heights and widths in accordance with this disclosure so long as the channel meets the design goals for capillarity, meaning that the movement of the liquid sample is facilitated from portion 60 toward reagent 20.

Cover 12 of biosensor 10 also includes secondary channels 64 carved on either side of flow channel 62. Each secondary channel 64 extends between ends 52, 54 and is defined by a floor 66 and walls 68 extending from floor 66. Walls 68 have a height that is less than the second height 44. In addition, an adhesive-dispense aperture 70 extends between floor 66 and surface 50. The height of walls 68 may also vary depending upon the overall thickness of cover 12, but generally ranges from about 8 $\mu$m to about 125 $\mu$m. Preferably, the height of walls 68 is from about 8 $\mu$m to about 75 $\mu$m, most preferably about 16 $\mu$m. It is appreciated that the shape and height of walls 68 may vary in accordance with this disclosure. Moreover, it is appreciated that cover 12 may be formed with greater or fewer than two secondary channels in accordance with this disclosure.

Bottom substrate 14 of biosensor 10 includes a first surface 22 that supports conductive tracks 16, 18 and an opposite second surface 24. See FIGS. 3–4. In addition, substrate 14 has opposite ends 26, 28 and edges 30, 32 extending between ends 26, 28. See FIG. 1. First end 26 includes a concave portion 76 that is formed with alignment with concave portion 60 of cover 12, to accommodate a user's finger. It is appreciated, however, that the design of portion 76 may vary in accordance with this disclosure. Bottom element 14 may be constructed from a wide variety of insulative materials. Non-limiting examples of insulative materials that provide desirable structural properties include glass, ceramics, vinyl polymers, polyimides, polyesters, and styrenics. Preferably, bottom element 14 is a flexible polymer, such as a polyester or polyimide. A non-limiting example of a suitable material is 5 mil thick KALADEX®, a polyethylene naphthalate film commercially available from E.I. DuPont de Nemours, Wilmington, Del., which is coated with gold by LPKF Laser Electronic GmbH, of Garbsen, Germany.

Biosensors 10 in accordance with the present invention are each formed to include a pre-defined reaction area 78 where the sensing takes place. When the biosensor is electrochemical, the pre-defined area is an electrochemical area that is located on a portion of the electrodes 16, 18. Referring now to FIG. 1, biosensor 10 includes an electrochemical reaction area 78, which is defined as the area of electrodes where reagent 20 is located. Recesses 34 are formed in substrate 14 of biosensor 10 and extend about area 78. It is appreciated that recesses 34 can take on any number of shapes and sizes in accordance with this disclosure. The method of forming recesses in substrate 14 is not limited. For example, the recesses may be formed by indenting, embossing, etching (e.g., using photolithographic methods or laser removal of a portion of the base material), or otherwise deforming or removing a portion of the base material. For a further description of the laser removal of suitable recesses, see U.S. Pat. No. 6,540,890 B1 entitled BIOSENSOR to Bhullar et al., which was filed in the U.S. Patent and Trademark Office on Oct. 6, 2000, the disclosure of which is expressly incorporated herein by reference.

As shown in FIG. 1, electrically conductive tracks 16, 18 are created or isolated on first surface 24 of bottom element 14. Tracks 16, 18 represent the electrodes of biosensor 10. As used herein, the phrase "electrode set" is a set of at least two electrodes, for example 2 to 200, or 3 to 20, electrodes. These electrodes may, for example, be a working electrode and an auxiliary electrode. Tracks 16, 18 cooperate to form an interdigitated electrode array 80 positioned within the periphery of recesses 34 and leads 82 that extend from array 80 and between recesses 34 toward end 28.

Tracks 16, 18 are constructed from electrically conductive materials. Non-limiting examples of electrically-conductive materials include aluminum, carbon (such as graphite), cobalt, copper, gallium, gold, indium, iridium, iron, lead, magnesium, mercury (as an amalgam), nickel, niobium, osmium, palladium, platinum, rhenium, rhodium, selenium, silicon (such as highly doped polycrystalline silicon), silver, tantalum, tin, titanium, tungsten, uranium, vanadium, zinc, zirconium, mixtures thereof, and alloys, oxides, or metallic compounds of these elements. Preferably, tracks include gold, platinum, palladium, iridium, or alloys of these metals, since such noble metals and their alloys are unreactive in biological systems. Most preferably, track 16 is a working electrode made of gold, and track 18 is an auxiliary electrode that is also made of gold and is substantially the same size as the working electrode.

Tracks 16, 18 are isolated from the rest of the electrically conductive surface by laser ablation. Techniques for forming electrodes on a surface using laser ablation are known. See, for example, U.S. patent application Ser. No. 09/411,940, filed Oct. 4, 1999, and entitled "LASER DEFINED FEATURES FOR PATTERNED LAMINATES AND ELECTRODE", the disclosure of which is expressly incorporated herein by reference. Tracks 16, 18 are preferably created by removing the electrically conductive material from an area extending around the electrodes. Therefore, tracks 16, 18 are isolated from the rest of the electrically-conductive material on substrate 14 by a gap having a width of about 25 $\mu$m to about 500 $\mu$m, preferably the gap has a width of about 100 $\mu$m to about 200 $\mu$m. Alternatively, it is appreciated that tracks 16, 18 may be created by laser ablation alone on bottom substrate 14. Further, tracks 16, 18 may be laminated, screen-printed, or formed by photolithography in accordance with this disclosure.

Multi-electrode arrangements are also possible in accordance with this disclosure. For example, it is contemplated that a biosensor may be formed that that includes an additional electrically conductive track (not shown). In a three-electrode arrangement, the first track is a working electrode, the second is a counter electrode, and the third electrode is a reference electrode. It is also appreciated that an alternative three-electrode arrangement is possible where tracks are working electrodes and a third electrode is provided as an auxiliary or reference electrode in accordance with this disclosure. It is appreciated that the number of tracks, as well as the spacing between tracks in array 80 may vary in accordance with this disclosure and that a number of arrays may be formed as will be appreciated by one of skill in the art.

Reagent 20 provides electrochemical probes for specific analytes and is applied onto bottom substrate 14 such that reagent 20 covers array 80. The choice of specific reagent 20 depends on the specific analyte or analytes to be measured, and are well known to those of ordinary skill in the art. An example of a reagent that may be used in biosensor 10 of the present invention is a reagent for measuring glucose from a whole blood sample. A non-limiting example of a reagent for measurement of glucose in a human blood sample contains 62.2 mg polyethylene oxide (mean molecular weight of 100–900 kilo Daltons), 3.3 mg NATROSOL 244M, 41.5 mg AVICEL RC-591 F, 89.4 mg monobasic potassium phosphate, 157.9 mg dibasic potassium phosphate, 437.3 mg potassium ferricyanide, 46.0 mg sodium succinate, 148.0 mg trehalose, 2.6 mg TRITON X-100 surfactant, and 2,000 to 9,000 units of enzyme activity per gram of reagent. The enzyme is prepared as an enzyme solution from 12.5 mg coenzyme PQQ and 1.21 million units of the apoenzyme of quinoprotein glucose dehydrogenase. This reagent is further described in U.S. Pat. No. 5,997,817, the disclosure of which is expressly incorporated herein by reference.

When hematocrit is to be determined, the reagent includes oxidized and reduced forms of a reversible electroactive compound (potassium hexacyanoferrate (III) ("ferricyanide") and potassium hexacyanoferrate (II) ("ferrocyanide"), respectively), an electrolyte (potassium phosphate buffer), and a microcrystalline material (Avicel RC-591F—a blend of 88% microcrystalline cellulose and 12% sodium carboxymethyl-cellulose, available from FMC Corp.). Concentrations of the components within the reagent before drying are as follows: 400 millimolar (mM) ferricyanide, 55 mM ferrocyanide, 400 mM potassium phosphate, and 2.0% (weight: volume) Avicel. A further description of the reagent for a hematocrit assay is found in U.S. Pat. No. 5,385,846, the disclosure of which is expressly incorporated herein by reference.

Non-limiting examples of enzymes and mediators that may be used in measuring particular analytes in sensor 10 of the present invention are listed below in Table 1.

TABLE I

| Analyte | Enzymes | Mediator (Oxidized Form) | Additional Mediator |
|---|---|---|---|
| Glucose | Glucose Dehydrogenase and Diaphorase | Ferricyanide | |
| Glucose | Glucose-Dehydrogenase (Quinoprotein) | Ferricyanide | |
| Cholesterol | Cholesterol Esterase and Cholesterol Oxidase | Ferricyanide | 2,6-Dimethyl-1,4-Benzoquinone 2,5-Dichloro-1,4-Benzoquinone or Phenazine Ethosulfate |
| HDL Cholesterol | Cholesterol Esterase and Cholesterol Oxidase | Ferricyanide | 2,6-Dimethyl-1,4-Benzoquinone 2,5-Dichloro-1,4-Benzoquinone or Phenazine Ethosulfate |

TABLE I-continued

| Analyte | Enzymes | Mediator (Oxidized Form) | Additional Mediator |
|---|---|---|---|
| Triglycerides | Lipoprotein Lipase, Glycerol Kinase, and Glycerol-3-Phosphate Oxidase | Ferricyanide or Phenazine Ethosulfate | Phenazine Methosulfate |
| Lactate | Lactate Oxidase | Ferricyanide | 2,6-Dichloro-1,4-Benzoquinone |
| Lactate | Lactate Dehydrogenase and Diaphorase | Ferricyanide Phenazine Ethosulfate, or Phenazine Methosulfate | |
| Lactate Dehydrogenase | Diaphorase | Ferricyanide | Phenazine Ethosulfate, or Phenazine Methosulfate |
| Pyruvate | Pyruvate Oxidase | Ferricyanide | |
| Alcohol | Alcohol Oxidase | Phenylenediamine | |
| Bilirubin | Bilirubin Oxidase | 1-Methoxy-Phenazine Methosulfate | |
| Uric Acid | Uricase | Ferricyanide | |

In some of the examples shown in Table 1, at least one additional enzyme is used as a reaction catalyst. Also, some of the examples shown in Table 1 may utilize an additional mediator, which facilitates electron transfer to the oxidized form of the mediator. The additional mediator may be provided to the reagent in lesser amount than the oxidized form of the mediator. While the above assays are described, it is contemplated that current, charge, impedance, conductance, potential, or other electrochemically indicated property of the sample might be accurately correlated to the concentration of the analyte in the sample with biosensor 10 in accordance with this disclosure.

A plurality of biosensors 10 are typically packaged in a vial, usually with a stopper formed to seal the vial. It is appreciated, however, that biosensors 10 may be packaged individually, or biosensors can be folded upon one another, rolled in a coil, stacked in cassette magazine, or packed in a blister packaging.

Biosensor 10 is used in conjunction with the following:

1. a power source in electrical connection with tracks 16, 18 and capable of supplying an electrical potential difference between the electrodes sufficient to cause diffusion limited electro-oxidation of the reduced form of the mediator at the surface of the working electrode; and 2. a meter in electrical connection with tracks 16, 18 and capable of measuring the diffusion limited current produced by oxidation of the reduced form of the mediator with the above-stated electrical potential difference is applied.

The meter will normally be adapted to apply an algorithm to the current measurement, whereby an analyte concentration is provided and visually displayed. Improvements in such power source, meter, and biosensor system are the subject of commonly assigned U.S. Pat. No. 4,963,814, issued Oct. 16, 1990; U.S. Pat. No. 4,999,632, issued Mar. 12, 1991; U.S. Pat. No. 4,999,582, issued Mar. 12, 1991; U.S. Pat. No. 5,243,516, issued Sep. 7, 1993; U.S. Pat. No. 5,352,351, issued Oct. 4, 1994; U.S. Pat. No. 5,366,609, issued Nov. 22, 1994; White et al., U.S. Pat. No. 5,405,511, issued Apr. 11, 1995; and White et al., U.S. Pat. No. 5,438,271, issued Aug. 1, 1995, the disclosures of which are expressly incorporated herein by reference.

Many fluid samples may be analyzed. For example, human body fluids such as whole blood, plasma, sera, lymph, bile, urine, semen, cerebrospinal fluid, spinal fluid, lacrimal fluid and stool specimens as well as other biological fluids readily apparent to one skilled in the art may be measured. Fluid preparations of tissues can also be assayed, along with foods, fermentation products and environmental substances, which potentially contain environmental contaminants. Preferably, whole blood is assayed with this invention.

After reaction is complete, a power source (e.g., a battery) applies a potential difference between electrodes. When the potential difference is applied, the amount of oxidized form of the mediator at the auxiliary electrode and the potential difference must be sufficient to cause diffusion-limited electro-oxidation of the reduced form of the mediator at the surface of the working electrode. A current measuring meter (not shown) measures the diffusion-limited current generated by the oxidation of the reduced form of the mediator at the surface of the working electrode. The measured current may be accurately correlated to the concentration of the analyte in sample when the following requirements are satisfied:

1. The rate of oxidation of the reduced form of the mediator is governed by the rate of diffusion of the reduced form of the mediator to the surface of the working electrode.

2. The current produced is limited by the oxidation of reduced form of the mediator at the surface of the working electrode.

To manufacture biosensor 10 a roll of metallized film is fed through guide rolls into an ablation/washing and drying station. A laser system capable of ablating substrate 14 is known to those of ordinary skill in the art. Non-limiting examples of which include excimer lasers, with the pattern of ablation controlled by mirrors, lenses, and masks. A non-limiting example of such a system is the LPX-300 or LPX-200 both commercially available from LPKF Laser Electronic GmbH, of Garbsen, Germany.

In the laser ablator, the metallic layer of the metallized film is ablated in pre-determined patterns, to form a ribbon of isolated electrode sets. The metallized film is further ablated, after the isolated electrode sets are formed to create recesses 34 positioned adjacent to each electrochemical area. The ribbon is then passed through more guide rolls, with a tension loop and through an optional optical or electrical inspection system. This inspection system is used for quality control in order to check for defects.

Reagent 20 is compounded and applied in a liquid form to the center of the electrochemical area at a dispensing and drying station. Reagent application techniques are well known to one of ordinary skill in the art as described in U.S. Pat. No. 5,762,770, the disclosure of which is expressly incorporated herein by reference. It is appreciated that reagent may be applied to the electrochemical area in a liquid or other form and dried or semi-dried onto the center of the electrochemical the electrochemical area in accordance with this disclosure.

In addition, a roll of cover material is fed into a laser ablator system as described above. In the laser ablator, the cover material is ablated in pre-determined channel patterns to form a ribbon of channel sets. Each channel set includes a flow channel 62 that is ablated to a depth of about 84 $\mu$m at first floor portion 36 and 16 $\mu$m at second floor portion 38. In addition, each channel set includes secondary channels 64 that are each ablated to a depth of about 16 $\mu$m. The cover material is then fed into a punching station where adhesive-dispense aperture 70 is punched through each secondary channel 64.

The ribbon of channel sets is unwound and fed into a sensor assembly station along with the reagent-coated bottom substrate. Cover 12 is placed on substrate 14 to cover reagent 20. Next, adhesive is dispensed through each aperture 70 into the secondary channels 64 while the cover 12 and substrate 14 are being compressed. It is appreciated that a number of commercially available dispense units may be used to apply the adhesive into apertures 70 in accordance with this disclosure. The assembled and time-cured material is then cut to form individual biosensors 10, which are sorted and packed into vials, each closed with a stopper, to give packaged sensor strips.

Although ablating channels 62, 64 is described herein, it is appreciated that the method of carving channels 62, 64 in cover 12 is also not limited. For example, the channels may be carved by etching (e.g., using photolithographic methods) or otherwise removing a portion of the surface of cover 12. In addition, the dimensions of the channels can vary based on the amount of sample to be analyzed and the surface area of the testing area.

The processes and products described above include disposable biosensor, especially for use in diagnostic devices. Also included, however, are electrochemical sensors for non-diagnostic uses, such as measuring an analyte in any biological, environmental, or other sample. As discussed above, biosensor 10 can be manufactured in a variety of shapes and sizes.

In use, a user of biosensor 10 places a finger on concave ends 60, 76. Capillary forces pull a liquid sample from ends 60, 76 through first portion 72 of channel 62. Walls 46 in first portion 72 of channel 62 converge as they approach second portion 74, increasing the capillary forces applied to the liquid sample. Thus, the liquid sample passes through the converging first portion 72 and encounters second portion 74 of channel 62 and reagent 20. Liquid sample dissolves reagent 20 and engages electrode array 78, where the electrochemical reaction takes place.

Referring now to FIGS. 6–9, biosensor 110 is provided in accordance with this invention. Biosensor 110 includes a cover 112, bottom substrate 114, and reagent 20. Biosensor 110 is preferably rectangular in shape. It is appreciated, however, that biosensor 110 can assume any number of shapes in accordance with this disclosure. Biosensor 110 is preferably produced from rolls of material. Thus, the selection of materials for the construction of biosensor 110 necessitates the use of materials that are sufficiently flexible for roll processing, but which are still rigid enough to give a useful stiffness to finished biosensor 110.

Cover 112 of biosensor 110 includes a first surface 148 facing substrate 114 and an opposite second surface 150. See FIGS. 6–7. In addition, cover 112 has opposite ends 152, 154 and edges 156, 158 extending between ends 152, 154. End 152 has a generally concave portion 160 that extends between edges 156, 158 in order to accommodate a user's finger. Cover 112 is preferably a polyester, a non-limiting example of which is 7 mil thick ST505 MELINEX® polyester film commercially available from E.I. DuPont de Nemours, Wilmington, Del.

Substrate 114 is similar to substrate 14, except that, upon assembly of biosensor 110, surface 22 is not completely coated with an electric conductor. Instead, surface 22 is exposed between about electrodes 16, 18. See, FIG. 6.

Figures 6, 7:
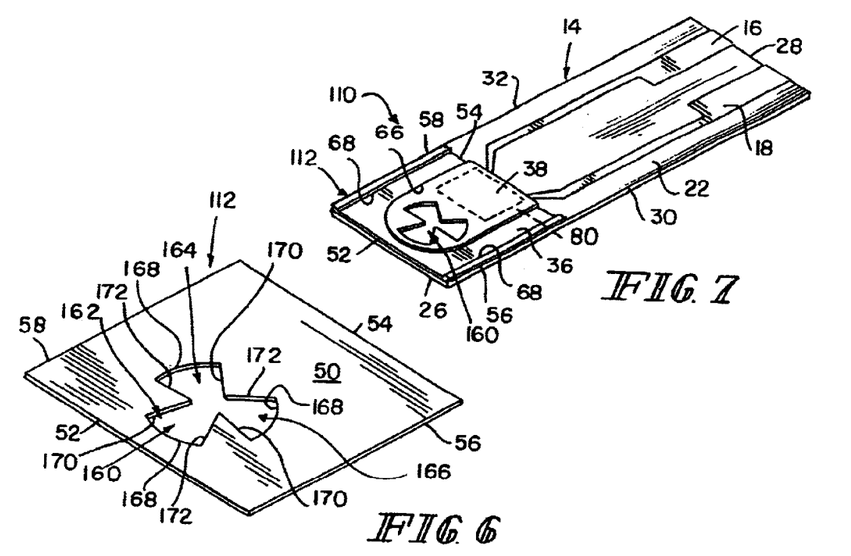
FIG. 6 is an exploded assembly view of a biosensor in accordance with another aspect of the invention, showing the biosensor including a substrate, a reagent, and cover.
FIG. 7 is a bottom perspective view of the cover of FIG. 6.
Figures 8, 9:
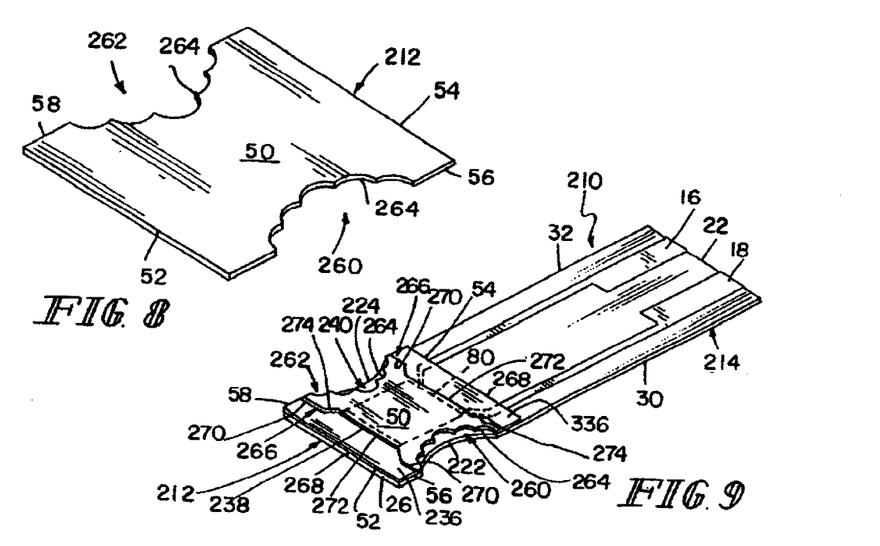
FIG. 8 is an end view of the biosensor of FIG. 6.
FIG. 9 is a view taken along lines 9—9 of FIG. 6.

Cover 112 is coupled to substrate 114 by an adhesive 116 that is coated on either substrate 114 or cover 112. Adhesive is preferably an adhesive as described above with reference to biosensor 10 or a thermoset adhesive. A non-limiting example of a suitable thermoset adhesive is a mixture of 95% wt./wt. of Item #38-868 polyurethane and 5% wt./wt. Item #38-8569 isocyanate both commercially available from National Starch& Chemical, a Member of ICI Group, Bridgewater, N.J. It is appreciated that cover 112 may be coupled to bottom substrate 114 using a wide variety of commercially available adhesives as well as heat sealing, or ultrasonic methods of joining cover 112 and substrate may be used to couple cover 112 and substrate 114 together in accordance with this disclosure.

Additionally, as shown in FIG. 7, a flow channel 162 is carved in first surface 148 of cover 112. Channel 162 extends between ends 152, 154. Channel 162 includes a first floor portion 136 and a second floor portion 138 define channel 162. Opposite walls 146 extend from first floor portion 136 and opposite walls 140 extend from second floor portion 138. First floor portion 136 and walls 146 define first portion 172 of channel and second floor portion 138 and walls 140 define second portion 174 of channel 162.

Walls 140 that extend from first floor portion 136 have a first height as shown by arrows 142 and walls 140 extending from second floor portion 138 have a second height as shown by arrows 144. First height 142 is greater than the second height 144, so that a liquid sample traveling in channel 162 encounters a greater capillary force as it enters second portion 174 of channel 162. Therefore, channel 162 acts to draw the liquid sample away from concave portion 160 and toward reagent 20 positioned spaced-apart from end 152. The height and width of first and second channel portions 136, 138 is similar to that of respective first and second portions 36, 38 of channel 38. It is appreciated that channel 162 may be formed with a single height, or that it may have a variety of heights in accordance with this disclosure.

To manufacture biosensor 110 a roll of metallized film is fed through guide rolls into an ablation/washing and drying station as described above with reference to biosensor 10. In the laser ablator, the metallic layer of the metallized film is ablated in pre-determined electrode patterns, to form a ribbon of electrode sets. The metallized film is further ablated to create recesses 34 positioned adjacent to each electrochemical area. The ribbon may be optically or electrically inspected as described above with reference to biosensor 10. Reagent 20 is dispensed on substrate 114 as described above with reference to biosensor 10. Additionally, the thermoset adhesive is coated substrate 114 on either side of area 78. It is appreciated that a number of commercially available dispense units may be used to apply the adhesive onto substrate 114 in accordance with this disclosure.

Further, a roll of cover material is fed into a laser system as described above with reference to biosensor 10. In the laser ablator, the cover material is ablated to form a row of spaced-apart channels 162. Each channel 162 is ablated to a depth of about 84 µm at a first floor portion 36 and 16 µm at a second floor portion 38. The cover material with spaced-apart rows of channels 162 is unwound and fed into a sensor assembly station along with the ribbon of reagent-coated bottom substrates.

The cover material is aligned with the ribbon of reagent-coated bottom substrates so that each cover 112 extends across each reagent 20. Next, a hot iron (not shown) of appropriate desirable shape and size is placed upon surface 150 of each cover 112 on either side of channel 162 to couple cover 112 and substrate 114 together. The assembled material is then cut to form individual biosensors 110, which are sorted and packed into vials, each closed with a stopper, to give packaged sensor strips.

The method of carving channel 162 in cover 112 is also not limited. For example, the channels may be carved by etching (e.g., using photolithographic methods) or otherwise removing a portion of the surface of cover 12. In addition, the dimensions of the channels can vary based on the amount of sample to be analyzed and the surface area of the testing area.

The processes and products described above include disposable biosensor, especially for use in diagnostic devices. Also included, however, are electrochemical sensors for non-diagnostic uses, such as measuring an analyte in any biological, environmental, or other sample. As discussed above, biosensor 110 can be manufactured in a variety of shapes and sizes.

In use, a user of biosensor 110 places a finger on concave ends 160, 76. Capillary forces pull a liquid sample from ends 160, 76 through first portion 172 of channel 162. Walls 146 in first portion 172 of channel 162 converge as they approach second portion 174, increasing the capillary forces applied to the liquid sample. Thus, the liquid sample passes through the converging first portion 172 and encounters second portion 174 of channel 162 and reagent 20. Liquid sample dissolves reagent 20 and engages electrode array 178, where the electrochemical reaction takes place.

Figure 10:
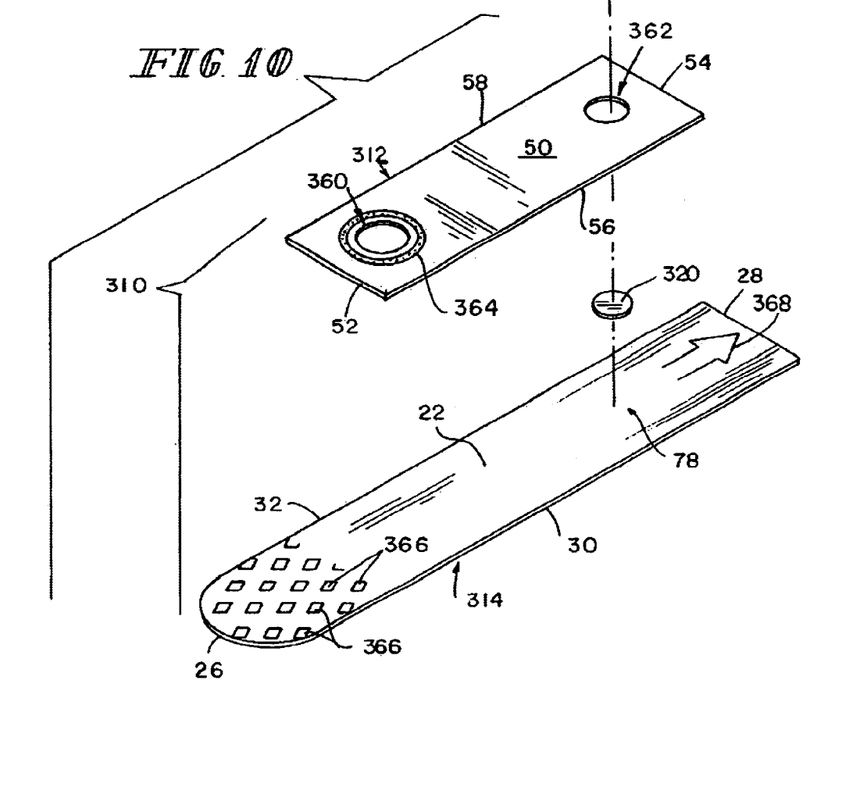
FIG. 10 is a perspective view of a biosensor in accordance with another aspect of the invention.
Figure 11:
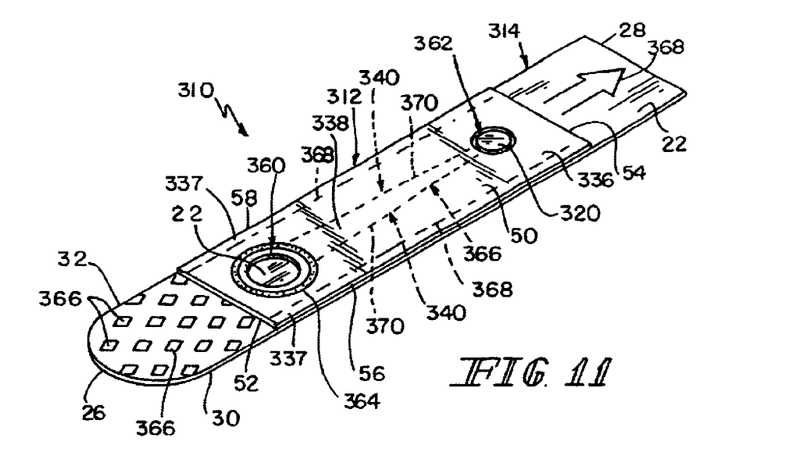

As shown in FIG. 10, a biosensor 210 is provided in accordance with another aspect of the present invention. Biosensor 210 includes a cover 212, a bottom substrate 214, and reagent 20. Biosensor 210 is preferably rectangular in shape and formed from materials that are similar to biosensors 10 and 110.

Cover 212 of biosensor 210 includes a flow channel 262 that is carved in first surface 48. Flow channel 262 extends between an opening 264 and an air vent 266. Substrate 214 supports tracks 16, 18 and reagent 20. Electrode array 78 and the reagent that covers array 78, is positioned to lie within channel 262 between opening 264 and air vent 266. Channel 262 is formed to have two floor portions having heights that are similar to channel 10. It is appreciated that channel 262 may be formed with a single height, or that it may have a variety of heights in accordance with this disclosure.

To manufacture biosensor 210 electrodes 16, 18 are formed on substrate 214, reagent 20 is applied to electrodes 16, 18 and thermoset adhesive is coated on substrate 214 in a manner similar to that described above with reference to biosensor 110.

Further, a roll of cover material is fed into a laser system as described above with reference to biosensor 10. In the laser ablator, the cover material is ablated to form a row of spaced-apart channels 262. Each channel 262 is ablated to a depth of about 84 µm at a first floor portion 36 and 16 µm at a second floor portion 38. The cover material with spaced-apart rows of channels 262 is unwound and fed into a sensor assembly station along with the ribbon of reagent-coated bottom substrates.

The cover material is aligned with the ribbon of reagent-coated bottom substrates so that each cover 212 extends across each reagent 20. Next, a hot iron (not shown) of appropriate desirable shape and size is placed upon surface 50 of each cover 212 on either side of channel 262 to couple cover 212 and substrate 214 together. The assembled material is then cut to form individual biosensors 210, which are sorted and packed into vials, each closed with a stopper, to give packaged sensor strips.

The method of carving channel 262 in cover 212 is also not limited. For example, the channels may be carved by etching (e.g., using photolithographic methods) or otherwise removing a portion of the surface of cover 212. In addition, the dimensions of the channels can vary based on the amount of sample to be analyzed and the surface area of the testing area.

The processes and products described above include disposable biosensor, especially for use in diagnostic devices. Also included, however, are electrochemical sensors for non-diagnostic uses, such as measuring an analyte in any biological, environmental, or other sample. As discussed above, biosensor 210 can be manufactured in a variety of shapes and sizes.

Although the invention has been described in detail with reference to a preferred embodiment, variations and modifications exist within the scope and spirit of the invention as described and defined in the following claims.

What is claimed is:

1. A method of forming a biosensor, the method comprising the steps of:
   providing a substrate and a cover including first and second surfaces,
   positioning a reagent on the substrate,
   carving a flow channel and at least one secondary channel by laser ablation in the first surface, and
   coupling the first surface of the cover to the second surface so that the flow channel is aligned with at least a portion of the reagent.

2. The method of claim 1, wherein the cover includes opposite ends and the carving step includes carving the flow channel to extend between the ends.

3. The method of claim 2, wherein a first portion of the channel is carved to have a first height and a second portion is carved to have a second height that is less than the first height.

4. The method of claim 3, wherein the first portion is carved to include side walls that converge from one of the ends toward the second portion of the flow channel.

5. The method of claim 1, further comprising the step of positioning an adhesive in the at least one secondary channel.

6. The method of claim 1, wherein at least one secondary channel is carved in the first surface on each side of the flow channel.

7. The method of claim 6, further comprising the step of positioning an adhesive in the secondary channels.

8. The method of claim 1, further comprising the step of positioning electrodes on the substrate.

9. The method of claim 8, wherein the electrodes are formed by laser ablation.

10. The method of claim 8, wherein the first surface of the cover is coupled to the channel so that the channel extends across at least a portion of the electrodes.

11. A method of forming a biosensor, the method comprising the steps of:
    providing a substrate and a cover including first and second surfaces,
    positioning a reagent on the substrate,
    carving a channel by laser ablation in the first surface, the channel including a first portion having a first height and a second portion having a second height that is less than the first height, and
    coupling the first surface of the cover to the second surface.

12. The method of claim 11, further comprising the step of positioning electrodes on the substrate.

13. The method of claim 12, wherein the electrodes are formed by laser ablation.

14. The method of claim 12, wherein the coupling step includes aligning the channel with the electrodes so that the channel extends across at least a portion of the electrodes.

15. The method of claim 11, wherein secondary channels are carved in the cover.

16. The method of claim 11, wherein the first portion is carved to include walls that converge toward the second portion of the channel.

17. A method of forming a biosensor, the method comprises the steps of:
    providing a substrate and a cover having first and second surfaces,
    applying a reagent onto the substrate to define a reaction zone,
    carving a channel by laser ablation in the first surface of the cover so that the channel includes at least one floor portion and walls extending from the at least one floor portion, and
    coupling the cover on the substrate so that the floor portion faces the substrate and the channel extends over at least a portion of the reagent.

18. The method of claim 17, further comprising the step of forming an electrode set in the reaction zone.

19. The method of claim 18, wherein the electrode set is formed by laser ablation.

20. The method of claim 17, wherein secondary channels are carved in the first surface of the cover.

* * * * *